United States Patent [19]

Yamaji et al.

[11] Patent Number: 4,583,861
[45] Date of Patent: Apr. 22, 1986

[54] SURFACE CONDITION JUDGING APPARATUS

[75] Inventors: Hiroshi Yamaji; Shigeru Ogawa; Katsuya Okumura, all of Yokohama, Japan

[73] Assignee: Tokyo Shibaura Denki Kabushiki Kaisha, Kawasaki, Japan

[21] Appl. No.: 404,899

[22] Filed: Aug. 3, 1982

[30] Foreign Application Priority Data

Aug. 12, 1981 [JP] Japan .............. 56-118790[U]
Dec. 26, 1981 [JP] Japan .................. 56-209509
Feb. 17, 1982 [JP] Japan .................... 57-22680

[51] Int. Cl.$^4$ ............................................ G01N 21/47
[52] U.S. Cl. ................................... 356/446; 356/448
[58] Field of Search ............... 356/445, 446, 447, 448, 356/343

[56] References Cited

U.S. PATENT DOCUMENTS

| | | | |
|---|---|---|---|
| 2,803,161 | 8/1957 | Summerhayes | 356/446 |
| 3,202,047 | 8/1965 | Lawler | 356/448 |
| 3,591,291 | 7/1971 | Greer | 356/448 |
| 3,770,351 | 11/1973 | Wyatt | 356/343 |
| 3,817,628 | 6/1974 | Adams | 356/448 |
| 3,874,799 | 4/1975 | Isaacs et al. | 356/236 |
| 3,922,093 | 11/1975 | Dandliker et al. | 356/448 |
| 3,984,189 | 10/1976 | Seki et al. | 356/446 |
| 4,184,082 | 1/1980 | Peoples | 356/446 |
| 4,299,497 | 11/1981 | Komodromos | 356/448 |
| 4,344,709 | 8/1982 | Provder et al. | 356/445 |
| 4,412,746 | 11/1983 | Yokouchi | 356/446 |

FOREIGN PATENT DOCUMENTS

| | | | |
|---|---|---|---|
| 466114 | 6/1950 | Canada | 356/446 |
| 53-46460 | 12/1978 | Japan. | |
| 56-121253 | 2/1980 | Japan. | |

OTHER PUBLICATIONS

Strobel, Howard A. *Chemical Instrumentation*, Addison-Wesley Publishing Company, Reading Mass. copyright 1960 p. 166.
The Catalogue of Tencor Instruments (USA); "Surfscan" (Wafer Surface Defect and Contamination Detector).
"Precision Measurement" by Y. Aoki; published by Corona, Inc. p. 335, Light Measuring Type Coarseness Measuring Device".

*Primary Examiner*—R. A. Rosenberger
*Attorney, Agent, or Firm*—Oblon, Fisher, Spivak, McClelland & Maier

[57] ABSTRACT

A parallel light beam having a predetermined diameter is projected onto an aluminum deposition film formed on a semiconductor wafer in a direction normal to the wafer surface. Light reflected by the aluminum deposition film is converted into reflected light intensity data by a plurality of photoelectric conversion elements arranged in a spherical surface with the center thereof at the center of the parallel light beam incidence spot. The reflected light intensity data are stored in a RAM in a microprocessor. The data stored in the RAM are displayed as a reflected light intensity distribution plot on a display unit for comparison with a standard reflected light intensity distribution plot, whereby the bonding property of the aluminum deposition film is judged.

9 Claims, 14 Drawing Figures

SURFACE CONDITION JUDGING APPARATUS

BACKGROUND OF THE INVENTION

This invention relates to an apparatus for judging the surface condition of a metal such as an aluminum film deposited on a semiconductor wafer.

To form an aluminum deposition film on a semiconductor wafer is an indispensable step in the manufacture of a semiconductor product. Between the surface of a pad made of such aluminum deposition film formed on a discrete semiconductor device or chip and an external terminal provided on a lead frame, thin aluminum or gold leads are bonded. The aluminum deposition film thus is required to always have a satisfactory bonding property with respect to aluminum or gold thin leads. The judgement of the bonding property usually has been made by visually inspecting the surface of the aluminum deposition film that is formed on a semiconductor wafer. The aluminum deposition film generally has a mirror like smooth surface, that is, its bonding property generally is satisfactory. If gas such as $CO_2$ remains in a deposition apparatus in the depositing step, the film deposited on the wafer has a rough surface, that is, its bonding property is deteriorated. This rough surface looks whitish and thus permits distinguishment of the unsatisfactory bonding property. However, a deposition film which has a satisfactory bonding property although its surface is whitish may be formed depending upon conditions at the time of the deposition. For example, when aluminum is deposited while maintaining a comparatively high wafer temperature or when it is deposited to a thickness in excess of 2 $\mu$m its crystal growth occurs on the wafer. The deposition film in this case has a whitish surface, but its bonding property is satisfactory. When the bonding property is judged by visual inspection, a surface of crystal growth is often rejected in spite of its satisfactory bonding property because its surface looks whitish.

SUMMARY OF THE INVENTION

An object of the invention is to provide a surface condition judging apparatus, which can accurately judge the surface condition of a metal such as an aluminum deposition film with respect to the bonding property thereof, the judgement being difficult by visual inspection.

According to the invention, the above object is attained by a surface condition judging apparatus, which comprises a housing for accommodating an inspection item in a state shielded against external light, light projecting means for projecting a parallel light beam onto the surface of the item in the housing in a direction at a predetermined angle to the surface of the item, photoelectric conversion means provided in a spherical surface having a predetermined radius and having the center located at a predetermined point on the surface of the item, for obtaining electric signals having magnitudes corresponding to the intensity of light reflected at said predetermined point of the item surface in directions of various reflection angles, an analog/digital converter for converting the electric signals from said photoelectric conversion means into digital signals, and an operational control section for obtaining a reflected light intensity distribution data representing the relation between the reflection angle and the intensity of reflected light from the digital signals and comparing the reflected light intensity distribution data with a standard reflected light intensity distribution data to thereby judge the surface condition of the inspection item.

DETAILED DESCRIPTION OF THE PREFERRED EMBODIMENTS

Figure 1:
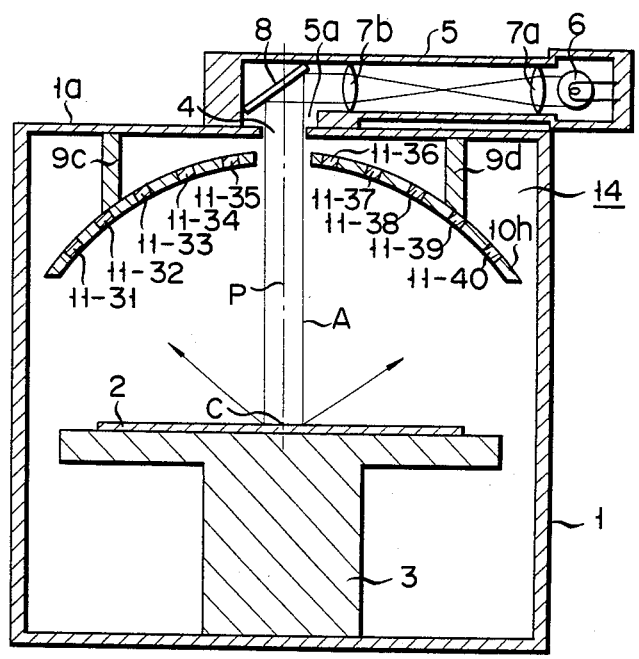
FIG. 1 is a schematic elevational sectional view showing one embodiment of the surface condition judging apparatus according to the invention.

The invention now will be described in detail in conjunction with preferred embodiments thereof with reference to the drawings. Referring to FIG. 1, there is shown a box-like housing 1, which can serve as a dark box to shield external light and is provided with a door (not shown). In the housing 1, a table 3 is provided on the bottom. A semiconductor wafer 2 having an aluminum film deposited thereon, the surface condition of which is to be judged, is horizontally set on the table 3. The semiconductor wafer 2 can be inserted into the housing 1 by opening the door mentioned above. The top wall 1a of the housing 1 is formed with a central see-through hole 4. A cylindrical optical unit 5 is mounted on top of the housing 1. The optical unit 5 has an opening 5a which communicates with the see-through hole 4 formed in the top wall 1a. In the optical unit 5, a light source lamp 6, lenses 7a and 7b and a mirror 8 are disposed in the mentioned order along a light path. Light emerging from the light source lamp 6 is converted through the lenses 7a and 7b into a parallel light beam A having a circular sectional profile. This light beam A is reflected by the mirror 8 to be directed through the opening 5a and see-through hole 4 into the housing 1 so that it is incident on the wafer 2 set on the table 3 in a direction normal to the wafer surface.

Figure 2:
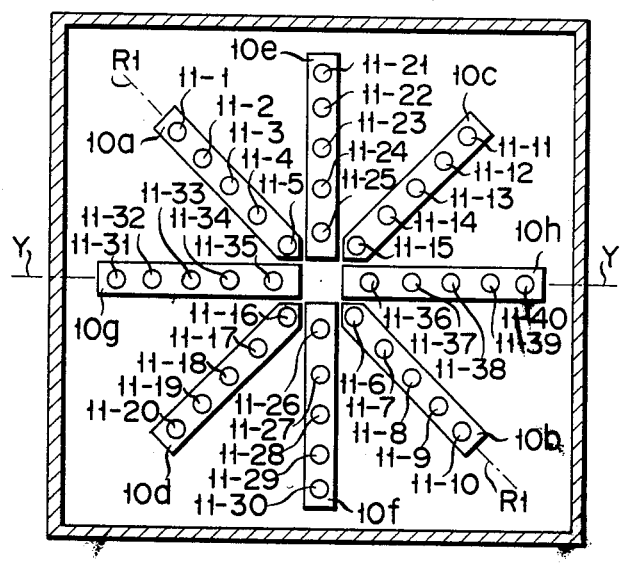
FIG. 2 is a plan view showing a photoelectric conversion unit in FIG. 1.

Eight arcuate supports 10a to 10h are secured to the inner surface of the top wall 1a of the housing 1 via mounting members 9a to 9h. As is shown in FIG. 2, the supports 10a to 10h are radially spaced apart by an equal angle of 45° with respect to a center position C. The center position C is the center of the spot of the parallel light beam A incident on the surface of the wafer 2 provided with an aluminum film in the normal direction thereto. The eight arcuate supports 10a to 10h lie in a spherical surface, the center of which is the center C of the incident light beam spot. The light beam A passes through a space defined by one end of the supports 10a to 10h. The supports 10a to 10h each supports five photoelectric conversion elements 11-i (i=1, 2, . . . , 40) such as photodiodes, phototransistors and solar batteries and the like. The individual photoelectric conversion elements 11-i have their light-receiving surfaces directed toward the incident light beam spot center C. The directions in which the photoelectric conversion elements 11-35 to 11-31 on the arcuate support 10g, for example, make respective angles of 10°, 20°, 30°, 40° and 50° with respect to the normal line P passing through the center C. The photoelectric conversion elements on the other arcuate supports 10a to 10f and 10h are similarly disposed.

Figure 3:
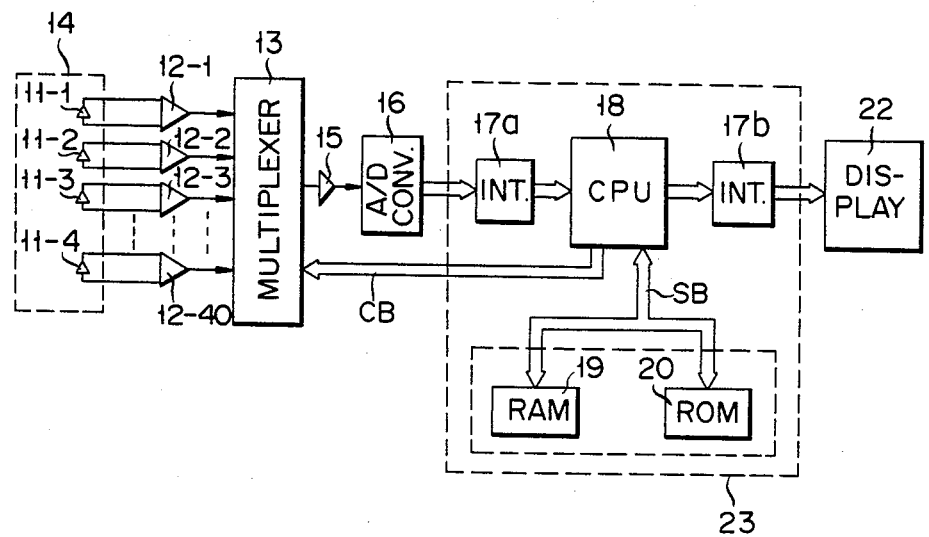
FIG. 3 is a block diagram showing the systematic electric circuitry of the embodiment of FIG. 1.

As shown in FIG. 3, output signals from the individual photoelectric conversion elements 11-i are amplified by respective amplifiers 12-i (i=1, 2, . . . , 40), and the amplified outputs are supplied to a multiplexer 13. The photoelectric conversion units 11-1 to 11-40 as a whole constitute a photoelectric conversion unit 14. The output of the multiplexer 13 is coupled through an amplifier 15 to an analog/digital (A/D) converter 16. The multiplexer 13 simultaneously receives the signals from the amplifiers 12-1 to 12-40 and sequentially supplies the received signals, for instance in the order of the signals from the amplifiers 12-1, 12-2, . . . , 12-40, to the amplifier 15 under the control of a central processing unit (CPU) 18 of a microcomputer hereinafter described.

Figure 4:
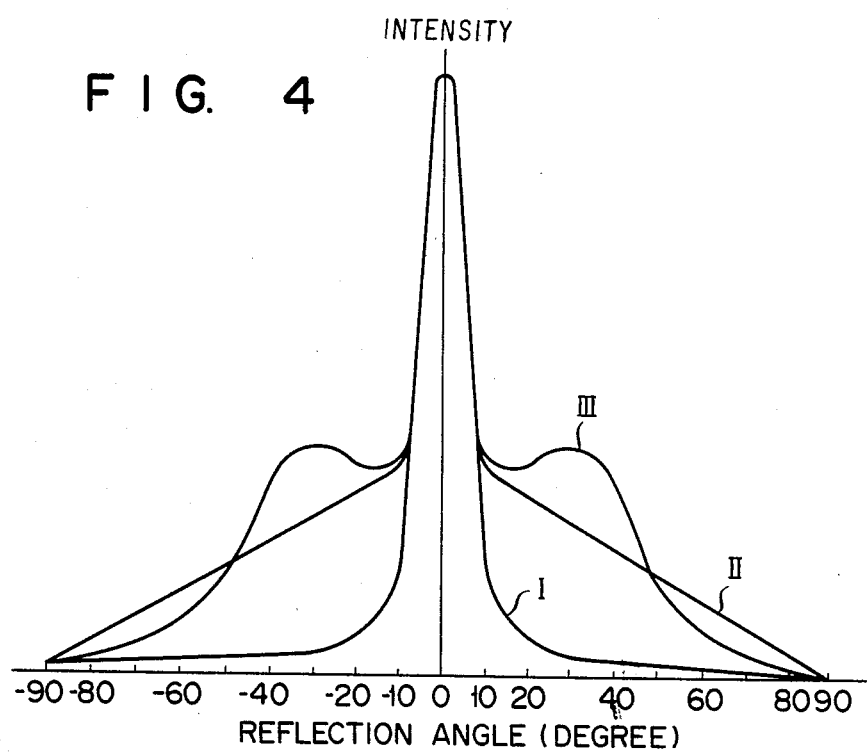
FIG. 4 is a graph showing reflected light intensity distribution plots obtained with different aluminum deposition films, which plots may be displayed on a display unit in the system of FIG. 3.

The A/D converter 16 produces digital signals having voltages corresponding to the intensities of light received by the photoelectric conversion elements 11-1 to 11-40. These digital signals are led through an interface 17a to the CPU 18. The CPU 18 supplies a switching control signal to the multiplexer 13 via a bus CB so that the signals from the individual photoelectric conversion elements 11-1 to 11-40 be sequentially supplied to the CPU 18. A random access memory (RAM) 19 and a read only memory (ROM) 20 are connected to the CPU 18 via a bus SB. Digital data representing the intensities of light received by the elements 11-i are sequentially stored in the RAM 19 in memory locations thereof specified by the CPU 18. In the ROM 20, data of preliminarily obtained, standard reflected light intensity distribution curves or plots as shown in FIG. 4 are stored. In FIG. 4, plot I is obtained with an aluminum deposition film having a mirror like smooth surface. Plot II is obtained with a film deteriorated from residual gas and having a whitish surface. Plot III is obtained with a crystal growth film having a whitish surface.

The operation of this embodiment will now be described with reference to FIGS. 1 to 4. First, the CPU 18 clears the RAM 19. The CPU 18 then supplies a switching control signal to the multiplexer 13. As a result, the output from the outermost photoelectric conversion element 11-1 on the arcuate support 10a is first supplied to the A/D converter 16, and the corresponding digital data is stored in the leading address memory location of the RAM 19. This first stored data represents the intensity of reflected light incident on the arcuate support 10a in a direction at an angle of 50° with respect to the normal line P. After the first data has been stored in the RAM 19, the multiplexer 13 is switched under the control of the control signal from the CPU 18 while at the same time the second address memory location of the RAM 19 is specified. As a result, data obtained from the output of the element 11-2 is stored in the second address memory location. Like, data corresponding to the outputs of the elements up to the element 11-40 are stored in the RAM 19.

After the data representing the intensities of reflected light incident on all the elements 11-1 to 11-40 have been stored in the RAM 19, the CUP 18 reads out the standard reflected light intensity distribution data as shown in FIG. 4 from the ROM 20 and displays the read-out data on a display unit 22. The CPU 18 then reads out the measurement data concerning the surface condition of the aluminum film deposited on the wafer 2, having been stored in the RAM 19, and produces a display plot from the read-out data. In the display plot producing process, the CPU 18 calculates the arithmetic mean value of the data obtained from the outputs of the elements 11-1, 11-20, 11-21 and 11-31, the light incidence angle of which is 50°, and plots the calculated value on the display unit 22 at a position corresponding to a reflection angle of −50°. The CPU 18 also calculates the arithmetic mean value of the data obtained from the outputs of the elements 11-10, 11-11, 11-30 and 11-40, the light incidence angle of which is again 50°, and plots the calculated value at a position corresponding to a reflection angle of +50°. Likewise, the CPU 18 plots the arithmetic mean values of the data for the elements on the supports 10a, 10d, 10e and 10g, which have the light incidence angles of 40°, 30°, 20° and 10°, at positions corresponding to reflection angles of −40°, −30°, −20° and −10°, and plots the arithmetic mean values of the data for the elements on the supports 10b, 10c, 10f and 10h, which have the incidence angles of 40°, 30°, 20° and 10°, at positions corresponding to reflection angles of +40°, +30°, +20° and +10°. In FIGS. 1 and 2, five photoelectric conversion elements 11-i are shown provided on each of the arcuate supports 10a to 10h to simplify the description. However, if nine photoelectric conversion elements with respective light incidence angles of 10°, 20°, 30°, 40°, 50°, 60°, 70°, 80° and 90° are provided on each arcuate support, comparison between each standard plot shown in FIG. 4 and the measurement data plot can be obtained over the entire reflection angle range. However, as is obvious from FIG. 4, a characterizing portion of each of the plots I to III resides in an angle range between 0° and 50°, so that judgement can be obtained sufficiently with the arrangement of FIGS. 1 and 2.

If the plot of the measurement data displayed on the display unit 22 closely resembles the standard plot I, it means that the surface of the aluminum film on the pertinent wafer 2 is a mirror surface having lustre. In this embodiment, no measurement data can be obtained for the reflection angle of 0° in FIG. 4 for no photoelectric conversion element is provided in a position on the path of the parallel light beam A. However, it can be readily estimated that the measurement data plot has a central portion having a very high peak value like the standard plot I. When the measurement data plot is like the plot I, the inspected aluminum deposition film can be judged to be normal and have satisfactory bonding property.

If the inspected aluminum deposition film is deteriorated by residual gas and has a whitish surface, the corresponding measurement data plot is like the standard plot II, with the intensity of reflected light gradually decreasing from the maximum value for the reflection angle of 0°. In this case, the bonding property of the deposition film surface is judged unsatisfactory.

If the inspected aluminum deposition film has a crystal growth surface, the surface is whitish like the surface of the deposition film deteriorated by residual gas. In this case, however, the corresponding measurement data plot is like the standard plot III, having maxima for reflection angles around ±20° to ±30°. The bonding property in this case is thus judged to be satisfactory in spite of the fact that the film has a whitish surface.

In the above arrangement, a mean values of the data obtained from the outputs of a plurality of elements 11-i with each definite light incidence angle has been calculated and plotted on the display unit 22. However, practically sufficient judgement of the deposition film surface can be obtained from a plot obtained directly from the data of the outputs of the elements 11-31 to 11-40 on line Y—Y in FIG. 2 over the reflection angle range between −50° and 50°.

In the meantime, the light intensity of the light source lamp 6, the input light intensity versus output voltage characteristic of the photoelectric conversion elements 11-i, the input versus output characteristic of the amplifiers 12-1 to 12-40, etc. are subject to changes in long use. The difference between the characteristics when the standard reflected light intensity distribution data on a calibration specimen are stored in the ROM 20 and the characteristics when the measurement is done on the same calibration specimen is obtained to correct the measurement data, thus allowing more accurate judgement. An equation for executing the correction may be stored in the ROM 20, and the CPU 18 may be adapted to effect the correction using the equation to obtain corrected data to the display 22.

First, before storing the standard data in the ROM 20, which may be a programmable ROM, the amplification factor of the amplifiers 12-1 to 12-40 is adjusted to make up for the fluctuations of the photoelectric characteristic of the photoelectric conversion elements 11-i and obtain a uniform photoelectric characteristic. When this adjustment is made, the outputs of the photoelectric conversion elements 11-i supplied to the multiplexer 13 have the same apparent level with the same light intensity.

Under this condition, a calibration specimen (not shown) is substituted for the inspection wafer 2 on the table 3. The calibration specimen is a white diffuser having a coating of barium sulfate or magnesium oxide powder. It diffuses the incident light substantially 100%. The diffused light is received by the photoelectric conversion elements 11-i. The intensities of light incident on the photoelectric conversion elements 11-i at this time are referred to as standard light intensities Xi. Data representing the standard light intensities Xi (i=1, 2, ..., 40) are stored in the ROM 20.

Next, the 100% diffuser is replaced with another 0% calibration specimen which has a mirror surface and regularly reflects incident light without any diffusion. At this time, the intensities of light incident on the photoelectric conversion elements 11-i are referred to as standard light intensities xi (i=1, 2, ..., 40). Data representing the standard light intensities xi are again stored in the ROM 20.

Figure 5:
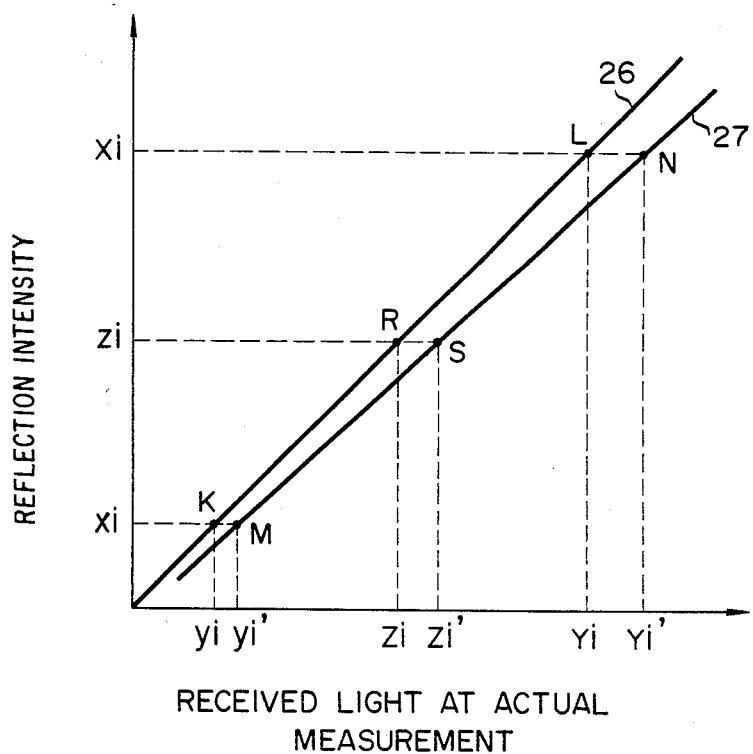
FIG. 5 is a graph showing a correction plot used for correcting measured light intensity data.

The data stored in the ROM 20, which were obtained using the 0% and 100% diffusion reflectors and represent the standard light intensities xi and Xi, are used as standard data. If there is subsequently no change in the characteristic of the individual elements such as amplifiers 12-1 to 12-40, the same data as the standard data would be obtained when calibration is made using the same 0% and 100% diffusion calibration specimens. Without any change in the characteristic of the elements, a plot 26 as shown in FIG. 5 is obtained. In the graph of the Figure, the ordinate is taken for the standard light intensity data xi and Xi stored in the ROM 20, and the abscissa is taken for the light intensity data yi and Yi obtained at the time of a subsequent calibration using the same calibration specimen. The plot 26 contains points K (xi, yi) and L (Xi, Yi) and has a slope angle of 45°. If subsequently there occurs any change in the characteristics of the elements, for instance a change in the light intensity of the light source lamp 6 and the gain of the amplifier 15, and/or the table 3 is tilted, different light intensity data yi' and Yi' would be obtained at the time of the subsequent calibration for the same calibration specimen. In this case, a plot 27 connecting points M (xi, yi') and N (Xi, Yi') results. This plot 27 is referred to as measurement data plot. If light intensity data Zi' is obtained in the subsequent measurement for the wafer 2, this data Zi' should be corrected to a data zi on the standard light intensity plot 26.

The measurement data plot 27 can be obtained from an equation $$zi = xi + \frac{Xi - xi}{Yi' - yi'}(Zi' - yi') \quad (1)$$

Since a co-ordinate point S (zi, Zi'), where zi is the standard data obtained under the standard condition and Zi' is the light intensity data obtained when the measurement is to be made, appears on the measurement data plot or a correction curve 27, the light intensity data Zi' which is subject to changes in long use, may be corrected to the corrected data zi being obtained under the standard condition.

Figure 6:
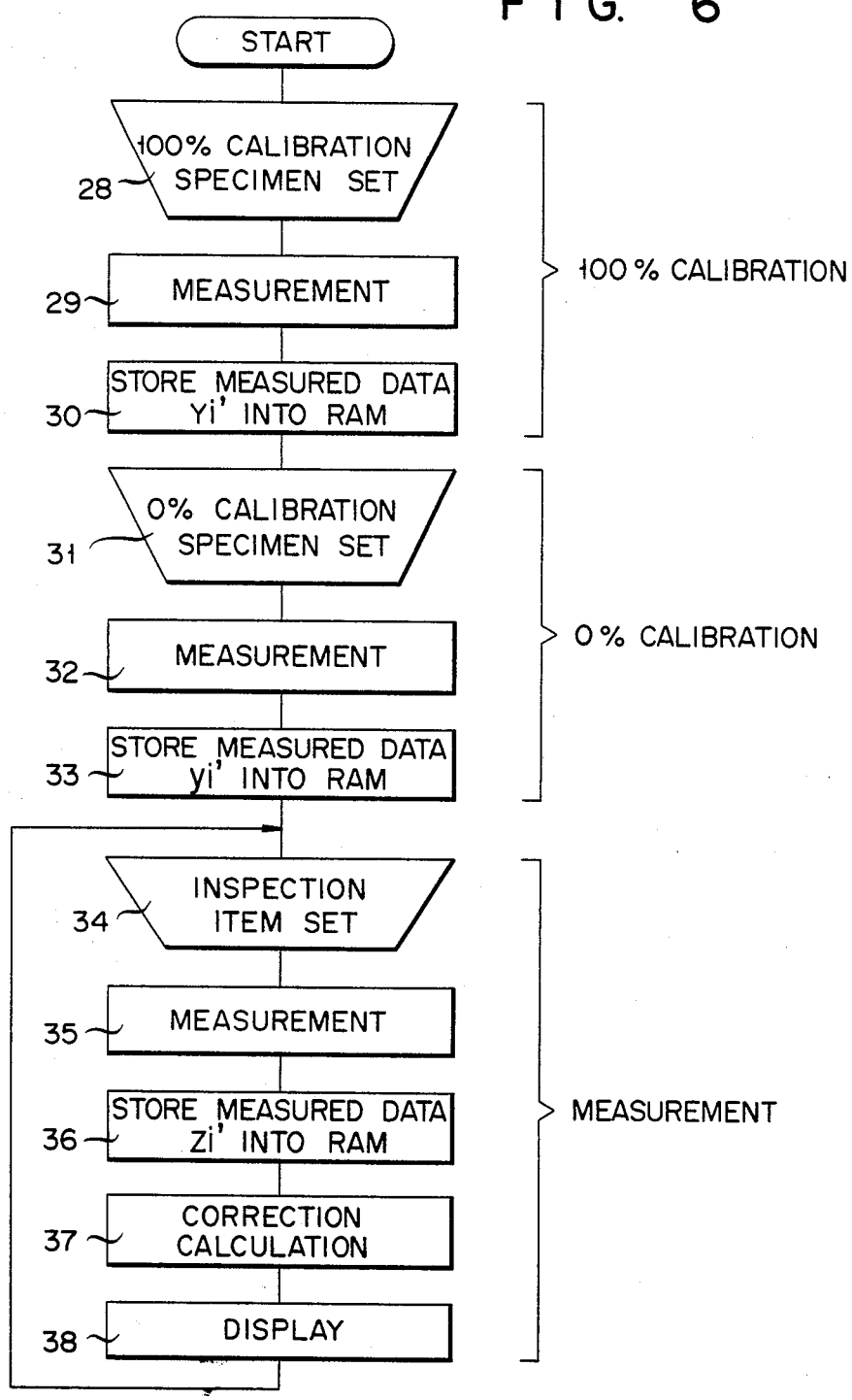
FIG. 6 is a flow chart illustrating the operation of the embodiment calibration is made.

FIG. 6 shows a flow chart illustrating the procedure of the correction. Prior to making the judgement of the surface condition of an aluminum deposition film the standard light intensity data xi, Xi are stored in the ROM 20. Then, the 100% diffusion calibration specimen is set on the table 3, in a step 28. Then, in a step 29 light from the light source lamp 6 is projected onto the 100% diffusion calibration specimen to obtain measurement data representing the intensities Yi' of reflected light incident on the photoelectric conversion elements 11-i. In a subsequent step 30, the Yi' measurement data are stored in the RAM 19. Thereafter, the 0% diffusion calibration specimen is set on the table 3 in a step 31. Measurement data representing the light intensities yi' is then obtained in a step 32. The obtained data yi' is stored in the RAM 19 in a step 33. Afterwards, the inspection wafer 2 is set on the table 3 in a step 34. Measurement data Zi' are obtained in a step 35. These data are stored in the RAM 19 in a step 36. In a subsequent step 37, the CPU 18 reads out a predetermined calculation program and standard light intensity data xi, Xi to obtain corrected data zi. The corrected data zi are obtained for all the photoelectric elements 11-i. These data Zi (i=1, ..., 40) are plotted on the display unit 22 in a step 38. The displayed measurement data plot is compared with the standard plots I to III as shown in FIG. 4. In this way, the judgement of the bonding property of the aluminum film deposited on the wafer 2 is effected.

While the calibration specimens having the diffusion factors of 100% and 0% have been used for the calibration described above, it is possible to use calibration specimens having different diffusion factors, for instance 80% and 20%, as well. Further, three or more calibration specimens having different diffusion factors may be used. In this case, the correction of the measurement data may be made by obtaining the measurement data plot using the least mean square method. Further, while in the above embodiment the judgement of the bonding property of the aluminum deposition film has been effected by an inspector from the reflected light intensity distribution plot displayed on the display unit 22, this is by no means limitative; the CPU 18 may be arranged to effect a processing for judgement as well following a judgement program which may be preliminarily stored in the ROM 20. At any rate, since the measurement data have been compensated for changes in conditions in the inspection from those at the time of obtaining the standard data stored in the ROM 20 before they are compared with the standard data, the accuracy of judgement can be extremely increased. Further, the photoelectric conversion elements 11-i may be provided not on the arcuate supports 10a to 10h but outside the housing 1 and connected to their respective light receiving positions inside the housing via optical fibers. Further, the elements 11-i can be arranged at any desired angles.

In the above embodiment, the inspection wafer 2 and photoelectric conversion unit 14 were held stationary. It is possible, however, to let the surface of the wafer 2 be scanned by the parallel light beam A, for instance with a movement of the table 3.

Figure 7:
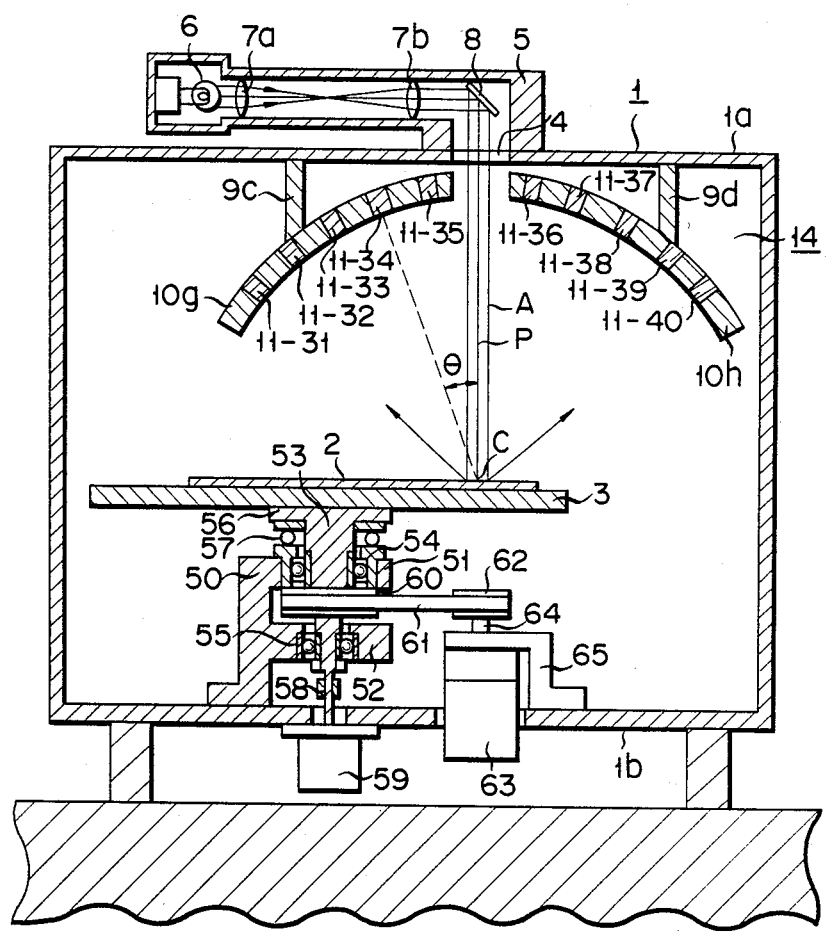
FIG. 7 is a schematic elevational sectional view showing a different embodiment of the invention.
Figure 8:
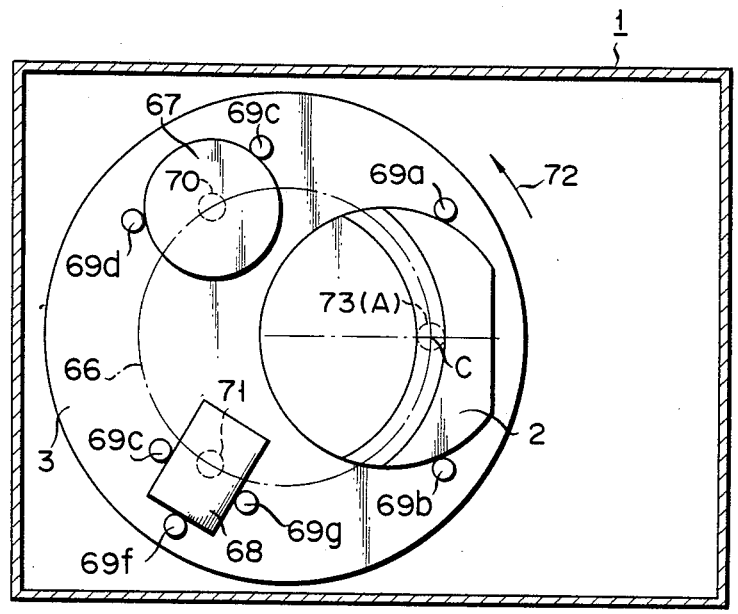
FIG. 8 is a plan view showing the positional relation among a semiconductor wafer and reference reflectors set on a table in the embodiment of FIG. 7.

This is realized in an embodiment shown in FIG. 7. In the Figure, the parts corresponding to those in FIGS. 1 and 2 are designated by like reference symbols. Referring to FIG. 7, a table 3 is mounted on top of a vertical shaft 53. The shaft 53 is journalled in bearings 54 and 55, which are mounted in respective upper and lower bearing support portions 51 and 52 of a support 50 which is in turn secured to the bottom of a housing 1. As shown in FIG. 8, the table 3 has a disc-like shape and is concentric with the shaft 53. The table 3 is supported on a top flange 56 of the shaft 53, and a thrust bearing 57 is provided between the flange 56 and the bearing 54.

A rotary encoder 59 which serves as a position detector is mounted on the outer surface of the bottom 1b of the housing 1. A shaft of the rotary encoder 59 is coupled by a shaft joint 58 to the lower end of the shaft 53. The shaft 53 has an integral pulley 60 which intervenes between the upper and lower bearings 54 and 55. The pulley 60 is coupled by an endless belt 61 to a pulley 62 which is mounted on a shaft 64 of a motor 63. The motor 63 is mounted on a motor support 65 which is secured to the bottom 1b such that its shaft 64 extends parallel to the shaft 53. Parallel light beam A from a lamp 6 is incident on the table 3 in the vertical direction parallel to the shaft 53. The center C of the incidence spot of the light beam A is spaced apart a predetermined distance from the center of the table 3.

A wafer 2 to be inspected is set on the table 3 such that it is found on a circular scanning orbit 66 which is traced by the circular incidence spot of the parallel light beam A when the table 3 is rotated as shown in FIG. 8. A 100% diffusion calibration specimen 67 and a 0% diffusion calibration specimen 68 are also set on the table 3 such that their centers are found on the circular scanning orbit 66. The wafer 2 and calibration specimens 67 and 68 are positioned by positioning pins 69a to 69g, and they are prevented by these positioning pins from being deviated by centrifugal forces exerted to them while the table 3 is in rotation. The calibration specimens 67 and 68 have substantially the same thickness as the wafer 2.

Figure 9:
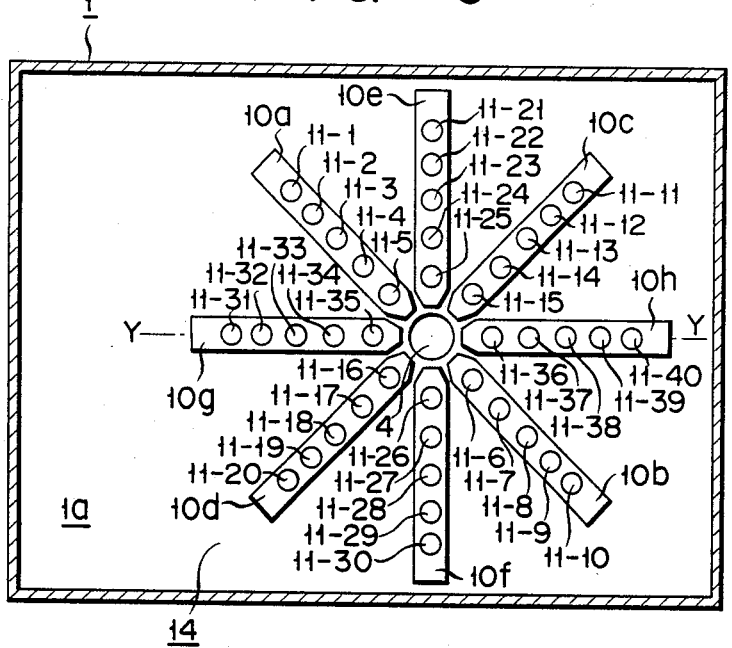
FIG. 9 is a plan view showing a photoelectric conversion unit in FIG. 8.

A photoelectric conversion unit 14, as shown in FIG. 9, is mounted on the inner surface of the top wall 1a of the housing 1 in the manner as described before in connection with FIG. 2.

Figure 10:
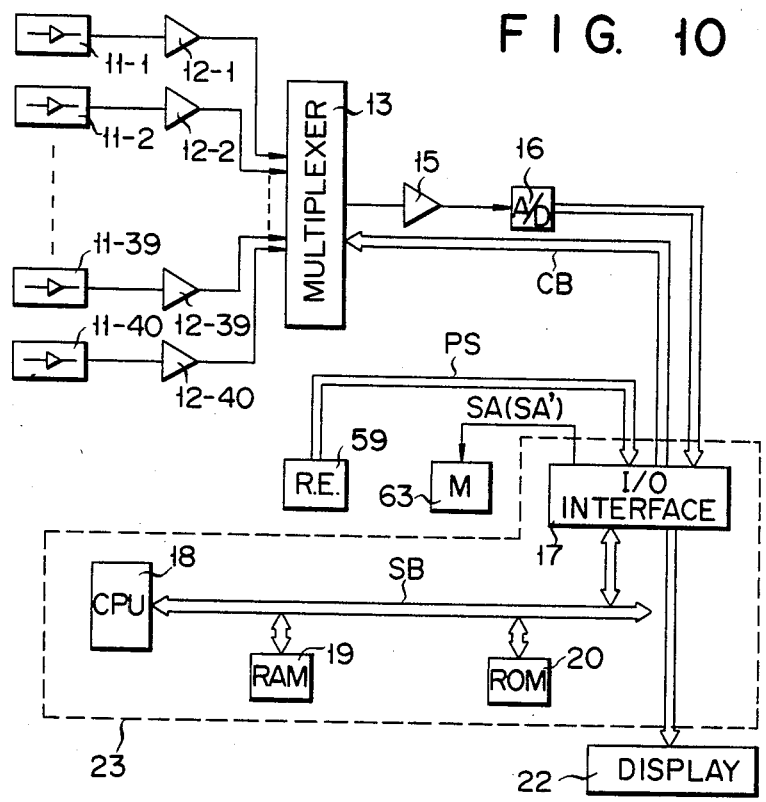
FIG. 10 is a block diagram showing the electric circuitry of the embodiment of FIG. 7.

FIG. 10 is a block diagram showing the electric circuitry of the embodiment of FIG. 7. In the Figure, the parts corresponding to those in FIG. 3 are designated by like reference symbols. Here, the output of an A/D converter 16 is supplied to a bus SB through an input-/output interface 17. A switching control signal to a multiplexer 13 is supplied from a CPU 18 through the input/output interface 17. The output of the rotary encoder 59 as the position detector is supplied to the CPU 18 through the input/output interface 17. A motor driving control signal from the CPU 18 is supplied to the motor 63 through the input/output interface 17.

The operation of this embodiment will now be described with reference to FIGS. 7 to 10.

First, the light intensity of the lamp 6, the gain of the amplifiers 12-1 to 12-40 and 15, the angle of the table 3 with respect to the parallel light beam A, etc. are adjusted to ideal or optimum conditions (which are hereinafter referred to as standard conditions). Under the standard conditions, the calibration specimens 67 and 68 are set on the table 3 in the housing 1 and properly positioned with the positioning pins 69c to 69g. Then, the motor 63 is driven to move the table 3 to a position to project the parallel light beam A onto each of the centers 70 and 71 of the calibration specimens 67 and 68 in the vertical direction. The intensities of reflected light incident on the photoelectric conversion elements 11-i are photoelectrically converted into electric signals of corresponding magnitudes. Digital values corresponding to these electric signals are stored in the ROM 20 in predetermined memory locations for the respective photoelectric conversion elements 11-i using a ROM writer (not shown). Of the stored data, those obtained with the 100% diffusion calibration specimen 67 are the standard light intensity data Xi (i=1, 2, ..., 40) while those obtained with the 0% diffusion calibration specimen 68 are the standard light intensity data xi. When carrying out the inspection of the wafer 2 later, the wafer 2 is set on the table 3 and properly positioned with the positioning pins 69a and 69b. Then, the parallel light beam A from the lamp 6 is projected onto the surface of the wafer 2. This is of course done with the housing 1 held in the state of a dark box. In this state, a measurement start signal is supplied to the CPU 18 through the input/output interface 17. As a result, the CPU 18 produces a control signal SA, which is supplied through the input/output interface 17 to the motor 63 to rotate the motor 63. The rotation of the motor 63 is transmitted to the shaft 53 via the endless belt 61, thus causing rotation of the table 3 about the shaft 53 in the direction of arrow 72 in FIG. 8. While the shaft 53 is being rotated, the rotary encoder 59 provides a rotational position signal PS which is supplied to the CPU 18 through the input/output interface 17. In the ROM 20, standard position data that are obtained when the centers 70 and 71 of the calibration specimens 67 and 68 and the region 73 of specimen 2 are in register with the path of the parallel light beam A, have been stored. The rotational position signal PS is instantaneously compared with these standard position data. When a coincidence of the compared data is detected, a strobe signal is supplied to the multiplexer 13 through a bus CB to actuate a selection switch therein. At the same time, the photoelectric conversion elements 11-i receive light reflected by the region 70, 71 or 73 and produce electric signals of magnitudes corresponding to the intensities of the incident light. These electric signals are amplified by the amplifiers 12-1 to 12-40 to be supplied as simultaneous signals to the multiplexer 13. The light intensity data concerning the light reflected by the region 70, 71 or 73 are thus sequentially coupled from the multiplexer 13 through the amplifier 15 to the A/D converter 16 for conversion into digital data. The digital data thus obtained are transferred through the input/output interface 17 to the CPU 18. The CPU 18 stores these data in the RAM 19 in memory locations for the individual photoelectric conversion elements 11-i. The data stored in the RAM 19 are the measurement data Yi' concerning the light reflected by the region 73 of the aluminum film formed on the wafer 2, the data Yi' concerning the light reflected from the region 70 of the 100% calibration specimen 67 and the data yi' concerning the light reflected from the region 71 of the 0% calibration specimen 68. When the storage of these data in the RAM 19 has been completed, a stop signal SA' is supplied to the motor 63 to stop the table 3. The conditions under which the inspection of the wafer 2 are carried out, i.e., the light intensity of the lamp 6, the gain of the amplifiers 12-1 to 12-40, the angle of the table 3, etc., may be different from the standard conditions as mentioned above. In this case, the measurement data Zi' are corrected to data zi as shown in FIG. 5 that would be obtained under the standard conditions. This is again done by the CPU 18. More particularly, the CPU 18 substitutes the standard data xi and Xi stored in the ROM 20 and the measurement data yi', Yi' and Zi' for each of the photoelectric elements 11-i stored in the RAM 19 into the equation (1) stored in the ROM 20 to obtain the corrected data zi which would be obtained under the standard conditions.

The corrected data zi calculated by the CPU 18 are stored in the RAM 19 and are also displayed as corrected measurement light intensity distribution plot on the display unit 22. In the ROM 20, standard light intensity distribution data, which were obtained with light reflected by a wafer having the "normal" deposition film in the measurement under the standard conditions, are stored. The plot of the standard data is displayed simultaneously with the measurement data plot on the display unit 22. The inspector thus can readily and accurately judge whether the inspected deposition film surface is "normal" or "rejected" from the comparison of shapes and levels of the two plots.

As has been described, with the above embodiment of the surface condition judging apparatus, in which a plurality of calibration specimens and the inspection wafer are held in the same plane such that they can be moved relative to the position of light incidence, the measurement data can be corrected to those that would be obtained under the standard conditions. Accurate and quick judgement of the surface condition, thus can be obtained from the comparison of the light intensity distribution plot based on the corrected measurement data and the standard light intensity distribution plot obtained under the standard conditions.

Figure 11:
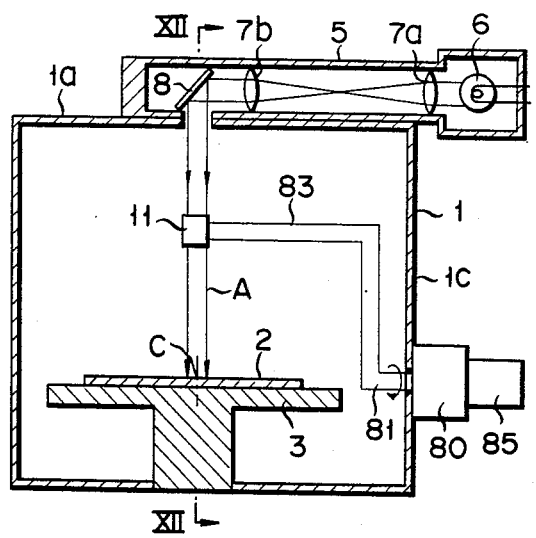
FIG. 11 is a schematic elevational sectional view showing a further embodiment of the invention.
Figure 12:
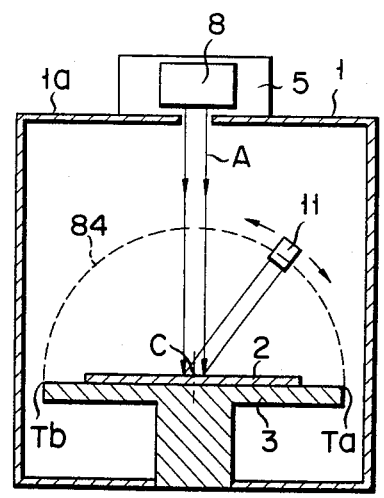
FIG. 12 is a schematic sectional view taken along line XII—XII in FIG. 11.
Figure 13:
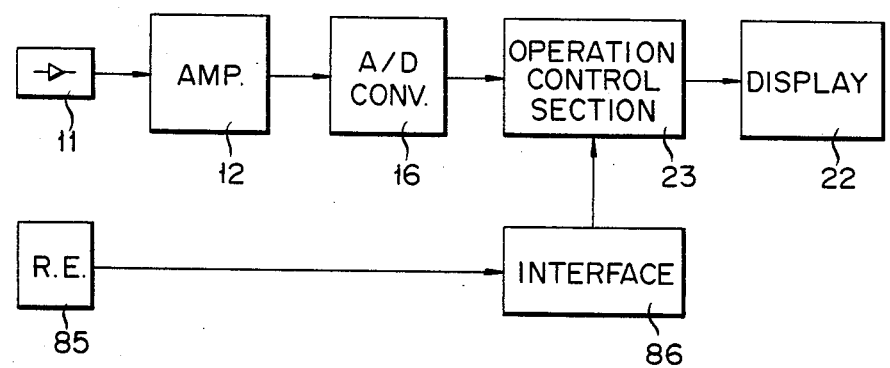
FIG. 13 is a block diagram showing the electric circuitry of the embodiment of FIG. 11.

In the preceding embodiments, a plurality of photoelectric elements 11-i have been disposed in a spherical surface with the center thereof at the center C of the incident light beam spot such that they have predetermined light incidence angles with respect to the normal line P passing through the center. FIGS. 11 to 13 show a further embodiment, which uses a single photoelectric conversion element which can be moved along an arcuate orbit with the center thereof at the incident light beam spot center C for obtaining measurement data. In the Figures, the corresponding parts to those in FIGS. 1 and 7 are designated by like reference symbols.

Referring to FIGS. 11 and 12, a motor 80 is mounted on one side wall 1c of a housing 1. The axis of the motor shaft 81 lies in the surface of a wafer 2 set on a table 3. A crankshaft 83 is coupled to the motor shaft 81. A photoelectric conversion element 11 is provided at the free end of the crankshaft 83. When the motor 80 is driven, the free end of the crankshaft 83 is moved along an arc 84 with the center thereof at the center C of the spot formed by the parallel light beam A. At the top of the arcuate orbit 84, the photoelectric conversion element 11 thus crosses the parallel light beam A. The motor 80 is provided with a rotary encoder 85 for detecting the rotational position. The encoder 85 provides a signal representing the angular position of the photoelectric conversion element 11 with respect to the parallel light beam A. As shown in FIG. 13, this signal is supplied to a CPU in an operation control section 23 through an interface 86.

In operation, assume that a start signal is supplied to the CPU in the section 23 when the photoelectric conversion element 11 is at a position Ta in FIG. 12. At this time, the motor 80 is not moved, and the encoder 85 is providing an angular position signal corresponding to +90°. A RAM memory location for this angular position is specified, and the output data from the photoelectric conversion element 11 is coupled through an amplifier 12 and an A/D converter 16 and stored in the specified memory location of the RAM. When this operation has been completed, a driving signal for driving the motor 80 for a predetermined angle, for instance 10°, is supplied from the CPU, thus moving the photoelectric conversion element to an angular position corresponding to +80°. A signal representing this angular position of 80° is supplied from the encoder 85 to the CPU through the interface 86. By this position signal the next RAM memory location is specified, and the output data of the element 11 at this time is stored in the specified memory location. In the above way, the operation of obtaining and storing light intensity data is carried out until data obtained when the element 11 is at a position Tb is stored. When this operation has been completed, the CPU reads out the data stored in the RAM and also the standard data stored in the ROM and supply these data to the display unit 22 for display so that the surface condition of the aluminum film deposited on the inspected wafer 2 may be judged.

The measurement operation described above has been based on a linear scanning, for instance along line Y—Y in FIG. 2. To cover a two-dimensional measurement scope as in the case of FIG. 2, the scanning from the position Ta to the position Tb in FIG. 12 may be carried out repeatedly with the table 3 at successive rotational positions. For example, after the scanning along the line Y—Y in FIG. 2 has been completed, the table 3 may be rotated by 45°. Now, the scanning can be made substantially along line R1—R1 in FIG. 2. This may be done until the entire scope is covered.

In the preceding embodiments, the parallel light beam A is directed to the surface of the wafer 2 in the normal direction. This permits obtaining substantially symmetrical reflected light data with respect to the normal line P as shown in FIG. 4 so that the judgement can be readily made. However, this is not essential in this invention, and the parallel light beam A may be made to be incident on the surface of the wafer 2 in a direction at an angle to the normal line P to the wafer surface.

Figure 14:
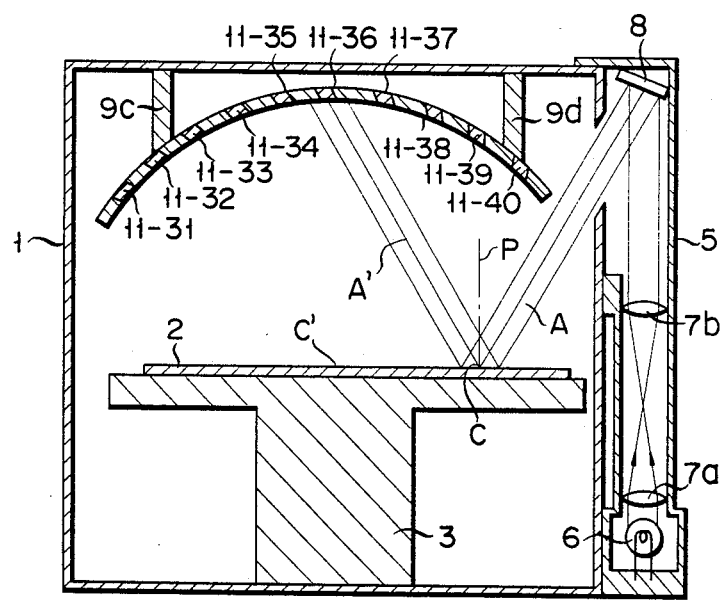
FIG. 14 is a schematic elevational sectional view of a still further embodiment of the invention.

FIG. 14 shows a further embodiment, in which the parallel light beam makes an angle of 30° with the normal line to the wafer surface. In the Figure, the parts corresponding to those in the preceding embodiments are designated by like reference symbols. Referring to FIG. 14, the parallel light beam A from the mirror 8 is incident on a wafer 2 in a direction at an angle of 30° with respect to the normal line P to the surface of the wafer 2. If the aluminum deposition film on the wafer 2 has a mirror surface, practically all the incident light is reflected in a direction at angle of 30° with respect to the normal line to be incident on the photoelectric unit 14. Here, however, the individual photoelectric elements 11-i are arranged in a spherical surface, the center C' of which is not the center C of the incident light beam spot. However, the light receiving surfaces of the elements 11-i are directed toward the incident light beam spot center C. Therefore, the light intensity distribution data obtained from the outputs of the photoelectric elements 11-31 and 11-40 disposed on the opposite sides of the axis of the reflected parallel light beam A' passing through the center C are not symmetrical with respect to this axis. However, if the standard light intensity distribution data stored in the ROM are obtained under the same conditions as in FIG. 4, sufficient judgement of the deposition film can of course be obtained from the measurement data plot displayed in superimposition upon the standard plot based on the standard data stored in the ROM.

What we claim is:

1. A method for evaluating a bonding property of an aluminum deposition film to which a metal bonding wire is to be bonded, comprising the steps of:
   projecting a light beam onto the surface of the aluminum deposition film deposited on a semiconductor substrate in a direction normal thereof;
   receiving a reflection from said surface of the aluminum deposition film at positions along a spherical surface with the center of the sphere located at the center of the incidence spot of the light beam and producing electric signals having magnitude corresponding to the intensity of the received reflection;
   obtaining a reflection intensity distribution curve by presenting the relationship between the intensity of the received reflection and the reflection angle defined between a normal line at said positions, said curve including a central reflection portion and diffusion reflection portions obtained at both sides of the central reflection portion; and
   comparing the reflection intensity distribution curve with standard intensity distribution curves which include a first curve having a central reflection portion with a very high peak value with respect to those diffusion reflection portions of low value obtained on both sides of the central reflection portion, a second curve having a central reflection portion with a peak value and monotonically decreasing diffusion reflection portions having relatively high values with respect to that of said diffusion reflection portions of the first curve, and a third curve having a central reflection portion with a peak value and diffusion reflection portions each having a peak value and having relatively high values with respect to that of said diffusion reflection portions of the first curve, respectively;
   thereby determining the bonding property to be satisfactory when the obtained curve is similar to either one of said first and second curves and being unsatisfactory when the obtained curve is similar to said second curve.

2. A method according to claim 1, which further comprises the steps of:
   setting said aluminum deposition film on a table in such state as to be shielded against external light;
   converting said electric signals into digital signals for obtaining reflection intensity distribution data through digital data processing; and
   calibrating said reflection intensity distribution data by using a reference diffusion factor calibration specimen.

3. A method according to claim 1, which further comprises the steps of:
   displaying said obtained reflection intensity distribution curve and said first to third standard intensity distribution curves on a display unit.

4. An apparatus for evaluating a bonding property of an aluminum deposition film to which a metal bonding wire is to be bonded, comprising:
   means for projecting a light beam onto the surface of the aluminum deposition film deposited on a semiconductor substrate in a direction normal thereof;
   means for receiving a reflection from said surface of the aluminum deposition film at positions along a spherical surface with the center of the sphere located at the center of the incidence spot of the light beam and for producing electric signals having magnitudes corresponding to the intensity of the received reflection;
   means for obtaining a reflection intensity distribution curve representing the relationship between the intensity of the received reflection and the reflection angle defined between a normal line at said positions, said curve including a central reflection portion and diffusion reflection portions obtained at both sides of the central reflection portion; and
   means for comparing the reflection intensity distribution curve with standard intensity distribution curves which include a first curve having a central reflection portion with a very high peak value with respect to those of diffusion reflection portions of low value obtained on both sides of the central reflection portion, a second curve having a central reflection portion with a peak value and monotonically decreasing diffusion reflection portions having relatively high values with respect to that of said diffusion reflection portions of the first curve, and a third curve having a central reflection portion with a peak value and diffusion reflection portions each having a peak value and having relatively high values with respect to that of said diffusion reflection portions of the first curve, respectively;
   thereby determining the bonding property to be satisfactory when the obtained curve is similar to either one of said first and third curves and being unsatisfactory when the obtained curve is similar to said second curve.

5. An apparatus according to claim 4, wherein said reflection receiving means includes a plurality of photoelectric conversion elements arranged at said positions along the spherical surface.

6. An apparatus according to claim 5, which further comprises:
a housing having a table on which said semiconductor substrate is set in such a state as to be shielded against external light; and
a plurality of arcuate supporting members for supporting said photoelectric conversion elements along said spherical surface;
and wherein said means for obtaining includes:
an analog/digital converter for converting the electric signals from said photoelectric conversion elements into digital signals; and
an operational control section for obtaining reflected light intensity distribution data representing a relation between the reflection angle and the intensity of reflected light from said digital signals for comparing said reflected light intensity distribution data with standard reflected light intensity distribution data to thereby judge the surface condition of the semiconductor wafer; said operational control section being a microcomputer including a central processing unit, a random access memory and a read only memory, said memories being connected to said central processing unit via a bus, said digital signals being stored in said random access memory under the control of said central processing unit, said standard reflected light intensity distribution data being preliminarily stored in said read only memory; the reflected light intensity distribution data read out from said random access memory and the standard reflected light intensity distribution data read out from said read only memory being simultaneously displayed on a display unit;
wherein said table is supported on a shaft rotatable by a motor, said light beam is incident on said table at a position thereof deviated from the axis of rotation of said table, a first diffusion factor calibration specimen, a second diffusion factor calibration specimen having a different diffusion factor from that of the first specimen and the aluminum deposition film on the semiconductor wafer are set on said table at respective different positions such that portions of said first and second specimens and said aluminum deposition film are found in a circular scanning orbit, so that they can be scanned by said light beam, and light intensity data of light reflected from the first and second diffusion factor calibration specimens and aluminum deposition film are sequentially stored in said random access memory.

7. An apparatus according to claim 4, wherein said reflection receiving means includes a single photoelectric conversion element mounted on a crankshaft and movable along an arcuate orbit crossing the axis of said light beam along said spherical surface.

8. An apparatus according to claim 7, wherein said reflection receiving means includes a motor for driving said crankshaft; and a rotary encoder for detecting the rotational position of said motor for determining said reflection angle.

9. An apparatus according to claim 4, wherein said metal bonding wire is made of aluminum or gold.

* * * * *